(12) United States Patent
Frerichs

(10) Patent No.: US 7,112,987 B2
(45) Date of Patent: Sep. 26, 2006

(54) SEMICONDUCTOR SENSOR WITH A FIELD-EFFECT TRANSISTOR

(75) Inventor: Heinz-Peter Frerichs, St. Peter (DE)

(73) Assignee: Micronas GmbH, Freiburg (DE)

( * ) Notice: Subject to any disclaimer, the term of this patent is extended or adjusted under 35 U.S.C. 154(b) by 0 days.

(21) Appl. No.: 10/862,833

(22) Filed: Jun. 7, 2004

(65) Prior Publication Data

US 2005/0035808 A1 Feb. 17, 2005

(30) Foreign Application Priority Data

Jun. 6, 2003 (DE) ............................... 103 25 718

(51) Int. Cl.
*G01R 31/26* (2006.01)
(52) U.S. Cl. .................... 324/769; 324/765; 324/158.1
(58) Field of Classification Search ...................... None
See application file for complete search history.

(56) References Cited

U.S. PATENT DOCUMENTS 4,411,741 A   10/1983   Janata ............................ 204/1
4,933,627 A * 6/1990   Hara ............................ 323/313
4,961,100 A * 10/1990  Baliga et al. ................ 257/172
5,449,939 A   9/1995   Horiguchi et al. ........... 257/360
5,543,649 A   8/1996   Kim et al. ................... 257/355
5,911,873 A   6/1999   McCarron et al. .......... 205/789

FOREIGN PATENT DOCUMENTS

DE   3123403        1/1983
DE   4333875        4/1995
EP   0 753 892 A1   1/1997
JP   2000187018 A * 7/2000

\* cited by examiner

*Primary Examiner*—Minh N. Tang
(74) *Attorney, Agent, or Firm*—O'Shea, Getz & Kosakowski, P.C.

(57) ABSTRACT

The semiconductor sensor has at least one field-effect transistor (31; 31, 32) which is coupled to a sensitive electrode and which has measuring phases that are interruptible by idle phases through a control device (50). During the idle phases, the field-effect transistor or transistors (30; 31, 32) together with their terminals is or are connected to the same potential, preferably the ground potential.

13 Claims, 3 Drawing Sheets

SEMICONDUCTOR SENSOR WITH A FIELD-EFFECT TRANSISTOR

BACKGROUND OF THE INVENTION

The present invention relates to the field of semiconductor sensors, and in particular to a semiconductor sensor with a field-effect transistor.

U.S. Pat. No. 5,911,873 describes the linking of field-effect transistors to measure ion concentrations in liquids and gases. U.S. Pat. No. 4,411,741 describes the determination of gas concentrations by measuring work function differences on gas-sensitive layers. German patent application DE 31 23 403 A1 describes a semiconductor sensor that can be switched by a control device from a measuring phase to an idle phase.

Also known are sensors in which one drain terminal and one source island are generated by counterdoping within one semiconductor substrate, and an insulating layer is grown or deposited on the substrate between the source terminal and the drain terminal. These sensors are also called transducers. Depending on the application, the ion-sensitive layer is applied, or a gas-sensitive layer is located at a predetermined distance, between the source terminal and the drain terminal. The latter types are often referred to as suspended gate FETs (SGFETs).

Another application using semiconductor sensors involves an electrode on the insulator that is capacitively controlled by a gas-sensitive gate incorporated at a predetermined distance and that is connected to the gate of a sensing transistor. In regard to the field-effect transistors used, these are so capacitively controlled field-effect transistors (CC-FET). German patent application DE 43 33 875 C2 describes such CC-FETs.

In semiconductor sensors using field-effect transistors, the change in the charge or work function caused by the ion to be detected is detected by a drain-source current change in the field-effect transistor that forms the sensing transistor. In the case of the SGFET and CC-FET, one specific advantage is the fact that the transducer and sensing layer can be processed independently of one other.

CC-FETs are also known in which a control electrode is incorporated under the floating electrode to affect the floating electrode capacitance, adjust the operating point, as required, and compensate for fabrication-related fluctuations in the operating characteristic of the field-effect transistor. A disadvantage of these systems is that the potential of the floating electrode is capacitively raised unintentionally. What always occurs is that this electrode is returned by non-controllable surface conductors to the potential of the environment, generally defined by a guard ring, and as a result, the field-effect transistor drifts in terms of its operating point. In other designs as well, a large fraction of the drift is caused by application of potentials to the source terminal, drain terminal, and substrate, the potentials being capacitively transmitted via the gate of the sensing transistor to the sensor electrode.

There is a need for a semiconductor sensor with improved operating point and reduced drift, especially when the semiconductor is turned on.

SUMMARY OF THE INVENTION

In a semiconductor sensor, a control device is provided by which the semiconductor sensor is switchable from its actual measuring phase to an idle phase within which all terminals of a field-effect transistor within the sensor are connected to the same potential.

The terminals of the field-effect transistor are switched to the same potential when not in the measuring phase (i.e., during an idle phase or in the turned-off state). For example, the terminals may be switched to ground potential by direct conductors or diodes. For example, the drain, source, and guard ring terminals, as well as the substrate and the sensor electrode, are connected to the same potential during the idle phase.

During a measuring phase, the potentials whose values are required for a defined operating point of the transistor are applied for a sufficiently short time to the substrate, the source terminal, and the drain terminal of the field-effect transistor. Subsequently during the idle phase, the terminals are connected to the same potential (e.g., ground).

In one embodiment, the sensor electrode of the semiconductor sensor is connected to two field-effect transistors of opposite doping states. In the idle phase, all the potentials are connected by a switching device to ground. In this embodiment, the measuring phase is divided into two partial measuring phases, whereby in the first partial measuring phase the potentials are applied, as described above, to one field-effect transistor, while in the second partial measuring phase the same potentials are applied with reversed signs to the second field-effect transistor. This embodiment has an advantage that the sum of the applied potentials integrated over time may be equal, or approximately zero, thereby preventing drift of the semiconductor sensor.

These and other objects, features and advantages of the present invention will become more apparent in light of the following detailed description of preferred embodiments thereof, as illustrated in the accompanying drawings.

DETAILED DESCRIPTION OF THE INVENTION

Unless otherwise indicated, components with the same reference notations have the same meaning. It must be noted here that, in the embodiments of the figures, field-effect transistors with concrete doping, that is, p-channel or n-channel field-effect transistors, are indicated. However, these examples are not to be construed as being restrictive. The scope of the invention also includes field-effect transistors of opposite polarity. It is simply noted that the potentials and terminals of the FET must then also be reversed.

Figure 1:
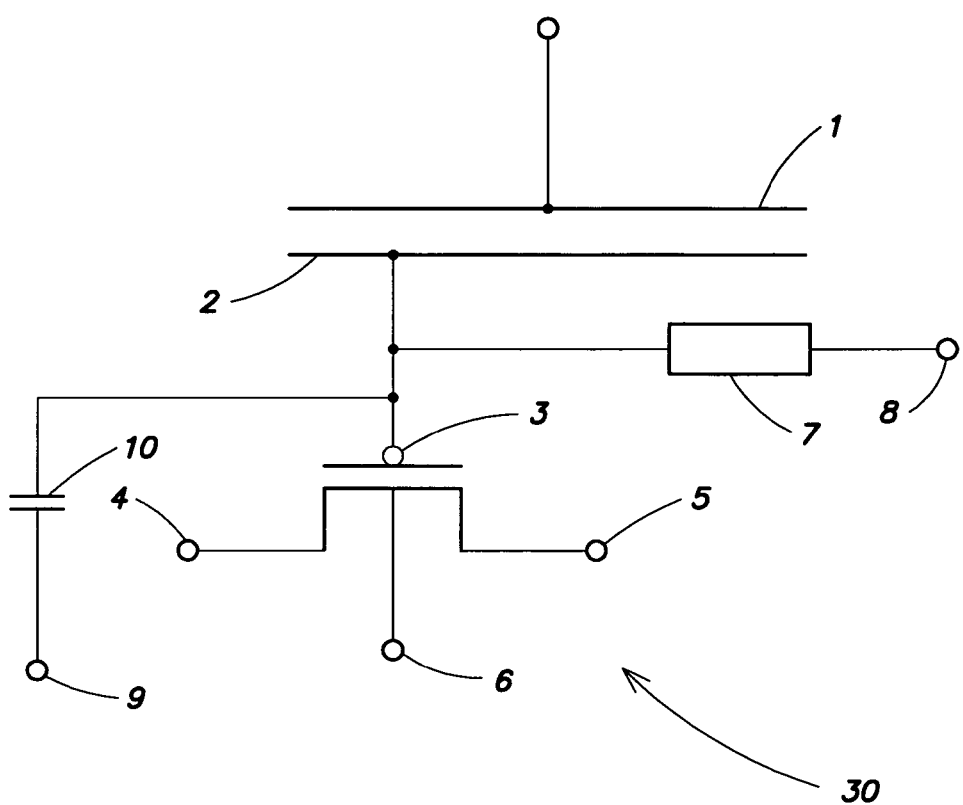
FIG. 1 is an equivalent circuit diagram of a prior art CC-FET.

FIG. 1 is an equivalent circuit diagram of a prior art capacitively controlled field-effect transistor 30 (CC-FET). The field-effect transistor 30 has a suspended sensitive gate 1, and a certain distance from the sensitive gate 1 is a counterelectrode 2 connected to a gate terminal 3. The field-effect transistor 30 is a p-channel field-effect transistor and has a drain terminal 4, a source terminal 5, and a substrate terminal 6 which in the present example is a substrate n-well terminal. A guard ring 8 is connected by a surface resistance 7 to the counterelectrode 2 and the gate terminal 3 of the field-effect transistor 30. Under the counterelectrode 2, the substrate 9 forms a capacitance 10 shown in the equivalent circuit diagram.

When the semiconductor sensor shown in FIG. 1 is operating, the individual terminals are connected to various predetermined potentials. The potentials at the drain terminal 4, the source terminal 5, and the substrate terminal n-well 6 are adjusted in such a way that an operating point is set for the field-effect transistor 30. Whenever such a semiconductor sensor is used to measure an ion concentration or a gas concentration, the change in the charge or work function caused by the ion or gas to be measured is detected by a drain-source current change at the field-effect transistor 30.

Figure 2:
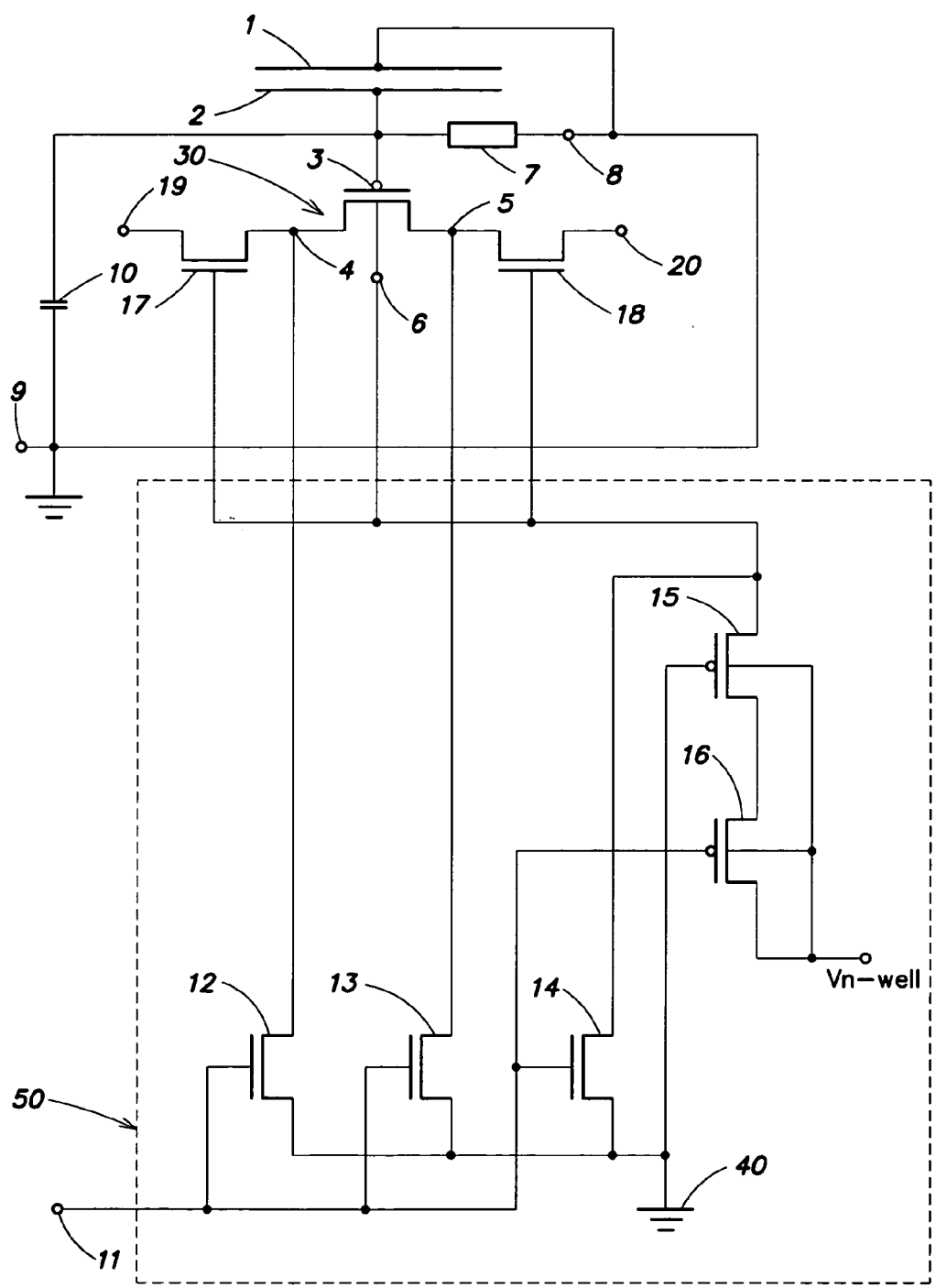
FIG. 2 shows the CC-FET of FIG. 1 together with a connected switching device that enables the CC-FET to be switched to a predefined potential during idle phases.

FIG. 2 illustrates the CC-FET of FIG. 1 together with a connected switching device that enables the CC-FET to be switched to a predefined potential during idle phases. To prevent the semiconductor sensor and its contained monolithic integrated field-effect transistor from drifting away from its desired operating point, a control device 50 is used to ensure that the semiconductor sensor is connected to a predefined potential during non-measurement times, that is, during idle phases or when turned off. The terminals of the field-effect transistor 30 of the semiconductor sensor are controllably connected to the same predefined potential, preferably ground potential 40 by the control device 50.

The semiconductor sensor illustrated in FIG. 1 has been augmented in FIG. 2 as follows. The drain terminal 4 of the field-effect transistor 30 is connected to the ground potential 40 through the load path of the field-effect transistor 12. The source terminal 5 of the field-effect transistor 30 is similarly connected to the ground potential 40 through a load path of field-effect transistor 13. Finally, the substrate terminal 6 is also connected through the load path of the field-effect transistor 14 to a reference potential 40, such as for example ground potential. The respective control terminals of the field-effect transistors 12, 13, and 14 are connected to each other, and to a control terminal 11 to which a control signal is applied. The control terminal 11 is also connected to a gate terminal of a p-channel field-effect transistor 16. The load path of the field-effect transistor 16 is connected in parallel with another p-channel field-effect transistor 15. The load paths of the two field-effect transistors 15, 16 are routed between the substrate terminal 6 and a pin to which a potential Vn-well is applied. The substrate terminals of the two p-channel transistors 15 and 16 are also connected to the pin to which potential Vn-well is applied. The gate terminal of the p-channel field-effect transistor 15 is connected to the ground potential 40. A decoupling transistor 17 together with its load path is connected between the terminal 19, to which the operating potential for the drain terminal 4 of the field-effect transistor 30 is to be applied, and the drain terminal 4 of the field-effect transistor 30. The gate terminal of the decoupling transistor 17 is connected to the substrate terminal 6. Another decoupling transistor 18 together with its load path is connected between the source terminal 5 of the field-effect transistor 30 and the terminal 20 to which the operating potential for the field-effect transistor 30 is applied. The control or gate terminal of the decoupling transistor 18 is also in contact with the substrate terminal 6.

Referring still to FIG. 2, the terminal of the sensitive gate 1 is connected together with the guard ring 8 to the substrate 9, and thus to the potential to which the drain terminal 4, the source terminal 5, and the substrate terminal n-well 6 of the FET 30 are connected during idle phases, as explained below. The functional principle of the semiconductor sensor shown in FIG. 2 including the control circuit 50 shall now be described.

When the semiconductor sensor is in the turned-off state, all the nodes are connected, either through wiring or diodes, to one potential—in this example, the potential of the substrate 9. When the semiconductor sensor is turned on, the drain terminal 4, the source terminal 5, and the substrate terminal n-well 6, are actively drawn to the ground potential through the transistors 12–16 in response to a voltage applied to the control terminal 11. The voltage applied to the control terminal 11 is selected in such a way that it is greater that the threshold voltage of the transistors 12, 13, and 14, and less than the inception voltage of the transistors 15 and 16. Decoupling transistors 17 and 18 ensure that the terminals 19 and 20 are isolated from the drain terminals 4 and the source terminals 5 of the field-effect transistor 30. The nodes are therefore at a defined, predetermined potential (e.g., ground potential).

To initiate the measurement action, a voltage is applied to the control terminal 11 during a measuring phase that is sufficiently short relative to the idle phase, the voltage being smaller than the threshold voltage of the transistors 12, 13, and 14 but greater than the threshold voltage of the transistors 15 and 16. The result is that the potentials applied to the drain terminal 19, to the terminal 20, and to the substrate terminal 6 are situated at the field-effect transistor 30, and the desired current that corresponds to the measurement parameter flows. At the end of the measuring phase, the idle phase is again initiated by applying a sufficiently large voltage to the control terminal 11 due to the fact that the voltage is selected to be greater than the threshold voltage of the field-effect transistor 30, with the result that all of the above-mentioned terminals are again drawn to the ground potential 40.

When the semiconductor sensor is operating, the measuring and idle phases are then repeated as often as desired. The control of the semiconductor sensor according to an aspect of the invention ensures that the field-effect transistor 30 operates within its desired operating point and that no drifting occurs.

Figure 3:
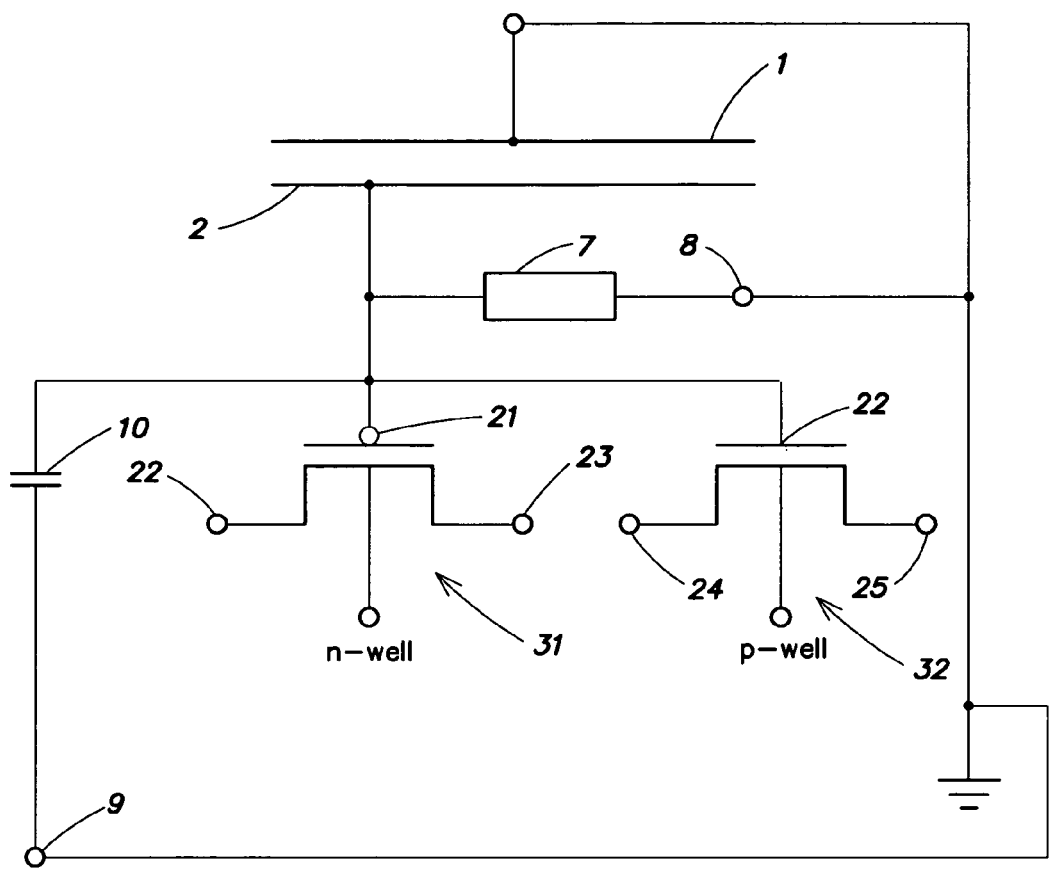
FIG. 3 shows another embodiment of a semiconductor sensor with a switching device, having two field-effect transistors with opposite doping.

Although, as presented above, the sensitive gate 1 and the guard ring 8 are permanently connected to the substrate 9 through an electrical connection, it is also possible to use an alternative design that also connects the two terminals 1 and 8 to the ground potential during the idle phases. FIG. 3 illustrates an alternative embodiment semiconductor sensor. In contrast to the embodiment of FIG. 2, the embodiment of FIG. 3 includes two field-effect transistors 31 and 32 with opposite doping. The reference notations already indicated identify components already known.

A p-channel field-effect transistor 31 together with its gate terminal 21 is connected to the counterelectrode 2. The second n-channel field-effect transistor 32 together with its gate terminal 22 is also connected to the counterelectrode 2. Both field-effect transistors 31 and 32 again have drain terminals 22 and 24, and source terminals 23 and 25.

This semiconductor sensor of FIG. 3 can also be operated with measuring phases and idle phases. In the idle phase, the potentials are again connected to ground potential. This action can be performed by a control device similar to that illustrated in FIG. 2. In this embodiment, however, the measuring phase described for FIG. 2 is divided into two partial phases. In the first partial measuring phase, the potentials are applied, as described above, to the p-channel field-effect transistor 31, while in a second measuring phase the same potentials are applied to the n-channel field-effect transistor 32, but with the signs reversed. This has the advantage that the sum of the applied potentials integrated over time is equal to zero, thereby preventing any drifting of the two transistors 31 and 32. The value of these potentials with opposite polarities is preferably based on the geometries of the transistors. The preferable approach involves capacitive coupling of the gate 1 by the transistor 31 at a value equal to the capacitive coupling of the gate 1 by the transistor 32.

In another variant for operating this circuit shown in FIG. 3, there is no differentiation between the idle and measuring phases, so that no control circuit is provided to initiate the idle phases. The semiconductor sensor of FIG. 3 can therefore be operated in such a way that it is always ready to effect measurements. Drifting of the operating point is prevented by the fact that two mutually complementary FETs 31 and 32 are coupled in parallel with their gate electrodes 21 and 22 to the sensitive gate 1. Due to the complementary arrangement of the system, the circuit node connected with the gate electrodes 21 and 22 is always at the same potential, which is the desired situation, in order to prevent the operating point of the system from drifting.

In FIG. 3, for the sake of clarity, possible additional transistors for switching the individual signals in the measuring phase have not been included in the drawing. What is critical in terms of the invention is simply the fact that in the idle phases all the potentials are at a predetermined potential, ground potential, for example, and the operating potentials are applied only in the measuring phase, whereby the measuring phase is preferably selected to be sufficiently small relative to the idle phases. The ratio of measuring phase to idle phases is, for example, 1:10, 1:100, or 1:1000.

The above embodiments referred in general to a sensitive gate 1. A gate of this type can be realized in a variety of ways. One way is, for example, to provide a liquid and a channel insulation below this. The channel insulation is located on a counterelectrode which is connected to the gate electrode or to the field-effect transistors. In another variant, the channel insulation is created by an air gap over which a sensitive electrode is located. The critical factor is always that this sensitive component of the semiconductor sensor be coupled to the gate terminal of the FET(s) in order to analyze the concentration of the ion/gas to be detected or measured.

Although the present invention has been shown and described with respect to several preferred embodiments thereof, various changes, omissions and additions to the form and detail thereof, may be made therein, without departing from the spirit and scope of the invention.

What is claimed is:

1. A semiconductor sensor, comprising:
   a field-effect transistor having a gate, a drain and a source, where the gate is coupled to a sensitive gate; and
   a control device that in an idle mode couples the drain and source to a common reference potential, and in a measuring mode couples the drain to a drain terminal and couples the source to a source terminal and in the measuring mode the source and drain terminals are at different potentials.

2. The semiconductor sensor of claim 1, where in the idle mode the drain terminal is coupled to the common reference potential through a first coupling field effect transistor and the source terminal is connected to the common reference potential through a second coupling field effect transistor.

3. The semiconductor sensor of claim 2, where the common reference potential is ground potential and the sensitive gate is configured as a suspended sensitive gate.

4. The semiconductor sensor of claim 3, where the field effect transistor comprises a p-channel field-effect transistor.

5. The semiconductor sensor of claim 3, further comprising:
   a guard ring that is connected to the gate of the field-effect transistor via a resistive element.

6. The semiconductor sensor of claim 5, where the guard ring is connected to the common reference potential.

7. The semiconductor sensor of claim 3, further comprising:
   a guard ring that is connected to the gate of the field-effect transistor via a resistive element and to the suspended sensitive gate.

8. The semiconductor sensor of claim 1, where the drain and the source of the field-effect transistor are switchable to the common reference potential by a plurality of switching transistors in response to the application of a control voltage to the plurality of switching transistors.

9. The semiconductor sensor of claim 8, where the drain and source of the field-effect transistor can be decoupled from terminals by decoupling transistors.

10. A semiconductor sensor, comprising:
    a field-effect transistor having a gate, a drain and a source, where the gate is coupled to a sensitive gate; and
    control means, in an idle mode for coupling the drain and source to a common reference potential, and in a measuring mode for coupling the drain to a drain terminal and couples the source to a source terminal and in the measuring mode the source and drain terminals are at different potentials.

11. The semiconductor sensor of claim 10, where in the idle mode the drain terminal is coupled to the common reference potential through a first switching element and the source terminal is connected to the common reference potential through a second switching element.

12. The semiconductor sensor of claim 11, where the first switching element comprises a first coupling field effect transistor and the second switching element comprises a second coupling field effect transistor.

13. The semiconductor sensor of claim 12, where the common reference potential is ground potential and the sensitive gate is configured as a suspended sensitive gate, and a guard ring is connected to the gate of the field-effect transistor and the suspended sensitive gate via a resistive element.

* * * * *